United States Patent [19]

Tucker

[11] Patent Number: 4,880,839
[45] Date of Patent: Nov. 14, 1989

[54] ACYANILIDE DERIVATIVES

[75] Inventor: Howard Tucker, Macclesfield, United Kingdom

[73] Assignee: Imperial Chemical Industries PLC, London, England

[21] Appl. No.: 62,691

[22] Filed: Jun. 16, 1987

[30] Foreign Application Priority Data

Jul. 18, 1986 [GB] United Kingdom ............... 8617652

[51] Int. Cl.$^4$ ............................................. A61K 31/65
[52] U.S. Cl. ..................................... 514/613; 558/413; 558/414; 560/250; 560/251; 560/106; 564/153; 564/154; 564/155; 564/156; 564/158; 564/162; 564/164; 564/166; 564/167; 564/169; 564/170; 514/616; 514/618; 514/619; 514/621; 514/622
[58] Field of Search ............... 514/613, 622, 616, 618, 514/619, 621; 564/162, 166, 167, 164, 169, 153, 154, 155, 156, 158

[56] References Cited

U.S. PATENT DOCUMENTS

| | | | |
|---|---|---|---|
| 3,875,229 | 4/1975 | Gold | 564/202 |
| 3,995,060 | 11/1976 | Neri et al. | 424/324 |
| 4,039,684 | 8/1977 | Berkman et al. | 424/324 |
| 4,191,775 | 3/1980 | Glen | 424/304 |
| 4,239,776 | 12/1980 | Glen et al. | 424/304 |
| 4,282,218 | 8/1981 | Glen et al. | 424/240 |
| 4,386,080 | 5/1983 | Crossley et al. | 564/170 |
| 4,535,092 | 8/1985 | Hughes | 514/438 |
| 4,636,505 | 1/1987 | Tucker | 514/256 |

FOREIGN PATENT DOCUMENTS

| | | |
|---|---|---|
| 0002309 | 10/1978 | European Pat. Off. . |
| 0002892 | 12/1978 | European Pat. Off. . |
| 0040932 | 5/1981 | European Pat. Off. . |
| 0079191 | 11/1982 | European Pat. Off. . |
| 0100172 | 7/1983 | European Pat. Off. . |
| 52-128329 | 10/1977 | Japan . |
| 1287753 | 9/1972 | United Kingdom . |

Primary Examiner—Robert T. Bond
Assistant Examiner—Amelia A. Owens
Attorney, Agent, or Firm—Cushman, Darby & Cushman

[57] ABSTRACT

An acylanilide of the formula:

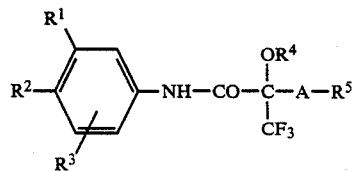

wherein $R^1$ or $R^2$ which may be the same or different, each is an electron-withdrawing substituent, alkylthio or phenylthio or $R^1$ is hydrogen, alkyl or alkoxy; wherein $R^3$ is hydrogen or halogen; wherein $R^4$ is hydrogen or acyl wherein A is branched-chain alkylene; and wherein $R^5$ is phenyl, substituted phenyl or naphthyl. The compounds possess progestational activity.

6 Claims, No Drawings

ACYANILIDE DERIVATIVES

This invention relates to new acylanilide derivatives which possess progestational activity.

Many acylanilides chemically-related to those hereinafter described are known to possess antiandrogenic activity. Of these, flutamide and hydroxyflutamide have been known for some considerable time, and others are described in Applicant's European Specifications Nos., 2309, 2892, 40932, 79191 and 100172.

We have now discovered that a small group of acylanilides surprisingly possess no antiandrogenic activity, but potent progestational activity.

According to the invention there is provided an acylanilide of the formula:

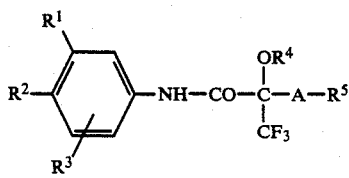

wherein $R^1$ is cyano, carbamoyl, nitro, fluoro, chloro, bromo, iodo or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each of up to 4 carbon atoms, or phenylthio, phenylsulphinyl or phenylsulphonyl; wherein $R^2$ is cyano, carbamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkysulphonyl each of up to 4 carbon atoms, or phenylthio, phenylsulphinyl or phenylsulphonyl; wherein $R^3$ is hydrogen or halogen; wherein $R^4$ is hydrogen or acyl of up to 15 carbon atoms; wherein A is branched-chain alkylene of up to 6 carbon atoms; and wherein $R^5$ is phenyl which bears one, two or three substituents selected from hydrogen, halogen, nitro, hydroxy, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or $R^5$ is naphthyl.

It will be observed that the acylanilide derivative of the invention possesses an asymmetric carbon atom, namely the carbon atom which bears the substituent $OR^4$, and it can therefore exist in racemic and optically-active forms. Furthermore, frequently the branched-chain alkylene group -A- will also possess an asymmetric carbon atom in which case pairs of diastereoisomers, in optically-active or racemic form, are also possible. It is to be understood that this invention encompasses any racemic form of the acylanilide derivative and any optically-active form which possesses progestational activity, it being a matter of common general knowledge how a racemic compound may be resolved into its optically-active forms and how any progestational activity present in any of these forms may be determined.

A suitable value for $R^1$ when it is alkyl, or for an alkyl substituent in $R^5$ when $R^5$ is phenyl substituted by alkyl is, for example, methyl or ethyl.

A suitable value for $R^1$ when it is alkoxy, or for an alkoxy substituent in $R^5$ when $R^5$ is phenyl substituted by alkoxy is, for example, methoxy or ethoxy.

A suitable value for $R^1$ or $R^2$ when it is alkanoyl, or for an alkanoyl substituent in $R^5$ when $R^5$ is phenyl substituted by alkanoyl is, for example, formyl or acetyl.

A suitable value for $R^1$ or $R^2$ when it is alkylthio, alkylsulphinyl, alkylsulphonyl, perfluoroalkyl, perfluoroalkylthio, perfluoroalkylsulphinyl or perfluoroalkylsulphonyl, or for such a substituent in $R^5$ when $R^5$ is phenyl bearing such a substituent is, for example, methylthio, ethylthio, methylsulphinyl, methylsulphonyl, trifluoromethyl, pentafluoroethyl, trifluoromethylthio, trifluoromethylsulphinyl or trifluoromethylsulphonyl.

A suitable value for $R^3$ when it is halogen, or for a halogen substituent in $R^5$ when $R^5$ is phenyl substituted by halogen, is fluoro, chloro, bromo or iodo.

$R^3$ is preferably hydrogen or chloro, especially hydrogen.

A suitable value for an alkoxycarbonyl or N-alkylcarbamoyl substituent in $R^5$ when $R^5$ is phenyl bearing such a substituent is, for example, methoxycarbonyl, ethoxycarbonyl or N-methylcarbamoyl.

A suitable value for $R^4$ when it is acyl is, for example, alkanoyl or aroyl each of up to 15 carbon atoms, for example acetyl, propionyl, decanoyl, dodecanoyl or benzoyl.

$R^4$ is preferably hydrogen,

A suitable value for A is, for example, 2-methylethylene or 2,2-dimethylethylene.

A preferred combination of values for $R^1$ and $R^2$ is as follows:

| $R^1$ | $R^2$ |
| --- | --- |
| trifluoromethyl | nitro |
| trifluoromethyl | cyano |
| chloro | chloro |
| chloro | nitro |
| chloro | cyano |
| cyano | cyano |
| nitro | cyano |
| ethoxy | nitro |
| chloro | methylsulphonyl |

A preferred acylanilide of the invention has the formula stated above wherein $R^1$ and $R^2$, which may be the same or different, each is cyano, nitro, trifluoromethyl, methylthio, methylsulphinyl, methylsulphonyl or chloro, $R^3$ and $R^4$ are both hydrogen, A is 2-methylethylene or 2,2-dimethylethylene and $R^5$ is phenyl which is unsubstituted or which bears one fluoro, chloro, hydroxy, methyl, nitro, methylthio, methylsulphinyl or methylsulphonyl substituent.

Specific acylanilides of the invention are hereinafter described in the Examples.

A particularly active compound is N-(2-hydroxy-4-phenyl-2-trifluoromethylpentanoyl)-4-nitro-3-trifluoromethylaniline in either of its diastereoisomeric forms.

The acylanilides of the invention may be manufactured by any chemical process known to be suitable for the manufacture of chemically-analogous compounds. A preferred process for the manufacture of an acylanilide of the invention comprises the reaction of an amine of the formula:

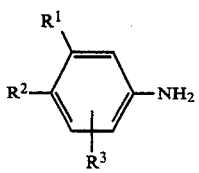

wherein $R^1$, $R^2$ and $R^3$ have the meanings stated above, with an acid of the formula:

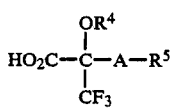

wherein $R^4$, $R^5$ and A have the meanings stated above, or with a reactive derivative of said acid.

A suitable reactive derivative of an acid is, for example, an acid anhydride, or an acyl halide, for example an acyl chloride, or a lower alkyl ester of said acid, for example the methyl or ethyl ester.

Preferably the reaction is carried out in N,N-dimethylacetamide solution using an acyl chloride (prepared from the acid and thionyl chloride) as reactant.

An acylanilide of the invention wherein $R^4$ is hydrogen may be prepared by the hydrolysis of the corresponding acylanilide wherein $R^4$ is acyl, and conversely, an acylanilide of the invention wherein $R^4$ is acyl may be prepared by the acylation of the corresponding acylanilide wherein $R^4$ is hydrogen.

An acylanilide of the invention wherein one or more of $R^1$, $R^2$ and a substituent in the phenyl group $R^5$ is alkylsulphinyl, perfluoroalkylsulphinyl or phenylsulphinyl, or is alkylsulphonyl, perfluoroalkylsulphonyl or phenylsulphonyl, may be prepared by the oxidation of the corresponding acylanilide wherein one or more of $R^1$, $R^2$ and a substituent in the phenyl group $R^5$ is alkylthio, perfluoroalkylthio or phenylthio, respectively. The oxidising agent and conditions used will determine whether a sulphinyl or a sulphonyl compound is obtained. Thus, oxidation with sodium metaperiodate in methanol solution at or below laboratory temperature will generally convert a thio compound into the corresponding sulphinyl compound; and oxidation with a peracid, for example m-chloroperbenzoic acid in methylene chloride solution at or above laboratory temperature will generally convert a thio compound into the corresponding sulphonyl compound.

A racemic acylanilide of the invention wherein $R^4$ is hydrogen may be separated into its optical isomers by forming an ester of the hydroxy group $OR^4$ with an optically-active acid, for example (−)-camphanic acid, separating the diastereoisomeric esters thus obtained, by fractional crystallisation or, preferably, by flash-chromatography, and then hydrolysis of each separate ester to the alcohol.

As stated above, an acylanilide of the invention possesses progestational properties as demonstrated by its ability to promote glandular development in the endometrium of an oestrogen-primed immature rabbit, the standard Clauberg assay procedure. An acylanilide of the invention may therefore be used as an oral contraceptive, and in the treatment of menstrual disorders, such as dysmenorrhea, dysfunctional bleeding and premenstrual tension, and in the treatment of hormone dependent tumours, especially those of the breast or endometrium. It may also be used for the synchronisation of oestrus and for the maintainence of early pregnancy in domestic animals such as cattle. At a dose of an acylanilide of the invention which produces progestational activity in rabbits no symptoms of toxicity are apparent.

The acylanilide of the invention may be administered to a warm blood animal in the form of a pharmaceutical or veterinary composition which comprises the acylanilide in association with a pharmaceutically-acceptable diluent or carrier.

The composition may be in a form suitable for oral dosage, as a tablet, capsule, aqueous or oily solution or suspension or emulsion. It may alternatively be in the form of a sterile solution or suspension suitable for patenteral administration, or be in the form of an ointment or lotion for topical administration or be in the form of a suppository for anal or vaginal administration.

The composition may additionally contain one or more drugs selected from oestrogens, for example, ethynyloestradiol or mestranol (which combination may be used as an oral contraceptive); antioestrogens, for example tamoxifen; androgens, for example cyproterone acetate and methyltestosterone; and gonadotrophin releasing factors and analogues thereof and antagonists thereof.

The acylanilide of the invention will normally be administered to a warm-blooded animal at a dose of between 0.1 mg. and 125 mg. per kg. bodyweight.

The invention is illustrated but not limited by the following Examples:

EXAMPLE 1

Thionyl chloride (0.82 ml.) was added dropwise to a stirred solution of 2-hydroxy-4-phenyl-2-trifluoromethylpentanoic acid (Isomer A, m.p. 145°–146° C.) in dimethylacetamide (60 ml.) which was maintained at −15° C. under an atmosphere of argon, the mixture was stirred at that temperature for 1 hour and 4-nitro-3-trifluoromethylaniline (1.9 g.) was added. The mixture was stirred at −15° C. for 1 hour and then at laboratory temperature for 20 hours, and was then poured into water (700 ml.). The mixture was extracted six times with diethyl ether (100 ml. each time) and the combined extracts were washed twice with aqueous 10% w/v sodium carbonate solution (50 ml. each time), dried over magnesium sulphate and evaporated to dryness. The residue was purified by flash chromatography on a silica gel column (Merck 9385) using a 2:1 v/v mixture of petroleum ether (b.p. 60°–80° C.) and ethyl acetate as eluant. There was thus obtained N-(2-hydroxy-4-phenyl-2-trifluoromethylpentanoyl)-4-nitro-3-trifluoromethylaniline, m.p. 162°–163° C. (more polar isomer).

The pentanoic acid used as starting material was obtained as follows:

1,1,1-Trifluoromethyl-4-phenylpentan-2-one (116.7 g.; b.p. 82°–83° C./10 mm. Hg.; prepared by the general process described in the Journal of Organic Chemistry, 1967, 32, 1316) was added dropwise to a cooled stirred solution of potassium cyanide (37.85 g.) in water (240 ml.) at such a rate that the temperature of the mixture was maintained at between 0° C. and 5° C. A 4:1 v/v mixture of water and concentrated sulphuric acid (300 ml.) was added at such a rate as to maintain the above temperature, and the mixture was stirred at laboratory temperature for 15 hours and then extracted four times with diethyl ether (90 ml. each time). The combined extracts were washed three times with water (100 ml. each time), dried over magnesium sulphate and evaporated to dryness under reduced pressure.

A mixture of the cyanhydrin thus obtained as a mixture of diastereoisomers (6.0 g.), concentrated aqueous hydrochloric acid (45 ml.) and glacial acetic acid (15 ml.) was vigorously stirred and heated at 100° C. for 48 hours, cooled and poured onto ice (125 g.). The mixture was extracted three times with diethyl ether (50 ml. each time) and the combined extracts were washed with water (50 ml.) and then extracted three times with saturated aqueous sodium carbonate solution (50 ml. each time). The combined extracts were acidified with concentrated aqueous hydrochloric acid and extracted three times with diethyl ether (50 ml. each time). The combined extracts were washed with water (50 ml.) and saturated aqueous sodium chloride solution (50 ml.), dried over magnesium sulphate and evaporated to dryness. The residue was stirred with petroleum ether (b.p. 60°–80° C.) and the mixture was filtered. There was thus obtained as solid residue Isomer A of 2-hydroxy-4-phenyl-2-trifluoromethylpentanoic acid, m.p. 145°–146° C. The petroleum ether filtrate was evaporated to dryness and there was thus obtained as residue a solid, m.p. 101°–102° C., which was predominantly Isomer B of 2-hydroxy-4-phenyl-2-trifluoromethylpentanoic acid contaminated with a small amount of Isomer A.

EXAMPLE 2

The process described in Example 1 was repeated using the impure Isomer B of the pentanoic acid (m.p. 101°–102° C.) as starting material in place of Isomer A. The product was purified by flash chromatography on silica gel (Merck 9385) using a 3:2 v/v mixture of petroleum ether (b.p. 60°–80° C.) and ethyl acetate as eluant, and the product obtained was crystallised from a 2:1 v/v mixture of ethyl acetate and petroleum ether (b.p. 60°–80° C.). There was thus obtained N-(2-hydroxy-4-phenyl-2-trifluoromethylpentanoyl)-4-nitro-3-trifluoromethylaniline, m.p. 145°–146° C. (less polar isomer).

What we claim is:

1. An acylanilide of the formula:

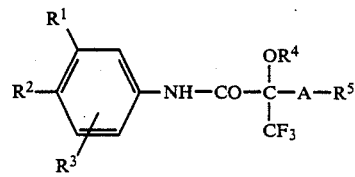

wherein $R^1$ is carbamoyl, nitro, fluoro, chloro, bromo, iodo or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each of up to 4 carbon atoms, or phenylthio, phenylsulphinyl or phenylsulphonyl; wherein $R^2$ is carbamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each of up to 4 carbon atoms, or phenylthio, phenylsulphinyl or phenylsulphonyl; wherein $R^3$ is hydrogen or halogen; wherein $R^4$ is hydrogen; wherein A is branched-chain alkylene of up to 6 carbon atoms; and wherein $R^5$ is phenyl which is unsubstituted or which bears one, two or three substituents selected from halogen, nitro, hydroxy, carboxy, carbamoyl and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or $R^5$ is naphthyl.

2. An acylanilide as claimed in claim 1, wherein $R^1$ and $R^2$, which may be the same or different, each is nitro, trifluoromethyl, methylthio, methylsulphinyl, methylsulphonyl or chloro, $R^3$ and $R^4$ are both hydrogen, A is 2-methylethylene or 2,2-dimethylethylene and $R^5$ is phenyl which is unsubstituted or which bears one fluoro, chloro, hydroxy, methyl, nitro, methylthio, methylsulphinyl or methylsulphonyl substituent.

3. The compound N-(2-hydroxy-4-phenyl-2-trifluoromethylpentanoyl)-4-nitro-3-trifluoromethylaniline in either of its diastereoisomeric forms.

4. A pharmaceutical or veterinary composition comprising an acylanilide as claimed in claim 1 in association with a pharmaceutically-acceptable diluent or carrier.

5. A composition as claimed in claim 4 which is in a form suitable for oral dosage, as a tablet, capsule, aqueous or oily solution or suspension or emulsion; or in the form of a sterile solution or suspension suitable for parenteral administration, or in the form of an ointment or lotion for topical administration or in the form of a suppository for anal or vaginal administration.

6. A method for producing a progestational effect in a warm-blooded animal, which comprises administering to said animal in need thereof an effective amount of at least one acylanilide as claimed in claim 1.

* * * * *